United States Patent [19]

Fields et al.

[11] Patent Number: 5,731,409
[45] Date of Patent: Mar. 24, 1998

[54] POLYPEPTIDES WITH TYPE I COLLAGEN ACTIVITY

[75] Inventors: Gregg B. Fields, Brooklyn Park; Leo T. Furcht; James B. McCarthy, both of Minneapolis, all of Minn.

[73] Assignee: Regents of the University of Minnesota, Minneapolis, Minn.

[21] Appl. No.: 330,599

[22] Filed: Oct. 28, 1994

[51] Int. Cl.$^6$ .............................. A61K 38/00; C07K 5/00; C07K 7/00; C07K 3/00

[52] U.S. Cl. ..................... 530/324; 530/300; 530/326; 530/327; 530/328; 530/345; 530/402

[58] Field of Search ........................... 530/300, 324, 530/326, 327, 328, 329, 330, 345, 402

[56] References Cited

U.S. PATENT DOCUMENTS

| | | |
|---|---|---|
| 4,578,079 | 3/1986 | Ruoslahti et al. . |
| 4,876,332 | 10/1989 | Tsilibary et al. . |
| 5,082,031 | 1/1992 | Tsilibary et al. . |
| 5,082,926 | 1/1992 | Chelberg et al. . |
| 5,152,784 | 10/1992 | Tsilibary . |

OTHER PUBLICATIONS

*The Proteins*, 3rd Ed., vol. IV, Academic Press, N.Y., pp. 468–495 (1979).
Bhatnagar, et al., *J. Cell Biol.*, 115, 442a (abstract #2569) (1991).
Cameron et al., *Invest. Ophthalmol Vis. Sci.*, 32, pp. 2766–2773 (1991).
Carter et al., *J. Cell. Biol.*, 110, pp. 1387–1404 (1990).
Carter et al., *J. Biol. Chem.*, 263, pp. 4193–4201 (1988).
Chapman et al., *Structural Aspects of Recognition and Assembly Biological Macromolecules*, pp. 387–401 (1981).
Chelberg et al., *J. Cell. Biol.*, 111, pp. 261–270 (1990).
Faassen et al., *J. Cell. Biol.*, 116, pp. 521–531 (1992).
Fields et al., *Synthetic Peptides: A User's Guide*, G.A. Grand, Ed., pp. 77–183 (1992).
Gullberg et al., *The EMBO Journal*, 11, pp. 3865–3873 (1992).
Gullberg et al., *J. Biol. Chem.*, 264, pp. 12686–12694 (1989).
Haugen et al., *J. Cell. Biol.*, 111, pp. 2733–2745 (1990).
Kleinman et al., *J. Biol. Chem.*, 253, pp. 5642–5646 (1978).
Kleinman et al., *Biochemical and Biophysical Research Communications*, pp. 426–432 (1976).
Koliakos et al., *J. Cell. Biol.*, 109, 200a (abstract #1080) (1989).
Kramer et al., *J. Biol. Chem.*, 264, pp. 4684–4688 (1989).
McCarthy et al., *J. Cell. Biol.*, 110, pp. 777–787 (1990).
Skaatz et al., *J. Biol. Chem.*, 266, pp. 7363–7367 (1991).
Wayner et al., *J. Cell. Biol.*, 105, pp. 1873–1884 (1987).
Wilke et al., *J. Invest. Dermatology*, 95, pp. 264–270 (1990).
Winkler et al., *J. Cell. Biol.*, 115, 442a (abstract #2568).
Oian et al., *FASEB J.*, vol. 7, A1306, 1992.

*Primary Examiner*—Avis M. Davenport
*Attorney, Agent, or Firm*—Merchant, Gould, Smith, Edell, Welter & Schmidt

[57] ABSTRACT

Polypeptides are provided that have a sequence of at least about four amino acids corresponding substantially to an amino acid sequence within the triple-helical domain of Type I collagen. The polypeptides promote cell adhesion and/or cell migration. Cell culture substrates coated with the polypeptides are also provided. Prosthetic devices and methods for identifying and distinguishing cells of different types are also provided.

24 Claims, 3 Drawing Sheets

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Gly  Pro  Lys  Gly  Ala  Ala  Gly  Glu  Pro  Gly  Lys  Pro
    1                   5                        10

( 2 ) INFORMATION FOR SEQ ID NO:2:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:2:

Gly  Lys  Arg  Gly  Ala  Arg  Gly  Glu  Pro  Gly  Pro  Ala
    1                   5                        10

( 2 ) INFORMATION FOR SEQ ID NO:3:

( i ) SEQUENCE CHARACTERISTICS:
        ( A ) LENGTH: 15 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:3:

Gly  Ala  Arg  Gly  Glu  Arg  Gly  Phe  Pro  Gly  Glu  Arg  Gly  Val  Gln
    1                   5                        10                       15

( 2 ) INFORMATION FOR SEQ ID NO:4:

( i ) SEQUENCE CHARACTERISTICS:
        ( A ) LENGTH: 12 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

Gly Ala Pro Gly Pro Lys Gly Ala Arg Gly Ser Ala
1               5                   10

(2) INFORMATION FOR SEQ ID NO:5:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:5:

Gly Lys Glu Gly Ser Lys Gly Pro Arg Gly Thr Thr
1               5                   10

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:6:

Gly Arg Asp Gly Ala Ala Gly Pro Lys Gly Asp Arg
1               5                   10

(2) INFORMATION FOR SEQ ID NO:7:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:7:

Gly Arg Pro Gly Glu Ala Gly Leu Pro Gly Ala Lys Gly Leu Thr
1               5                   10                  15

(2) INFORMATION FOR SEQ ID NO:8:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (xi) SEQUENCE DESCRIPTION: SEQ ID NO:8:

Gly Ala Lys Gly Asp Arg Gly Asp Pro Gly Pro Lys
1               5                   10

(2) INFORMATION FOR SEQ ID NO:9:

(i) SEQUENCE CHARACTERISTICS:
        (A) LENGTH: 9 amino acids
        (B) TYPE: amino acid
        (D) TOPOLOGY: linear (ii) MOLECULE TYPE: peptide (xi) SEQUENCE DESCRIPTION: SEQ ID NO:9:

Gly Asp Arg Gly Met Lys Gly His Arg
1               5

(2) INFORMATION FOR SEQ ID NO:10:

( i ) SEQUENCE CHARACTERISTICS:
  ( A ) LENGTH: 12 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:10:

```
Gly Pro Val Gly Pro Ala Gly Lys Asn Gly Asp Arg
 1           5                   10
```

( 2 ) INFORMATION FOR SEQ ID NO:11:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:11:

```
Gly Arg Pro Gly Pro Ala Gly Pro Pro Gly Ala Arg Gly Gln Ala
 1           5                   10                  15
```

( 2 ) INFORMATION FOR SEQ ID NO:12:

( i ) SEQUENCE CHARACTERISTICS:
  ( A ) LENGTH: 15 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:12:

```
Gly Ala Arg Gly Pro Ala Gly Pro Gln Gly Pro Arg Gly Asp Lys
 1           5                   10                  15
```

( 2 ) INFORMATION FOR SEQ ID NO:13:

( i ) SEQUENCE CHARACTERISTICS:
  ( A ) LENGTH: 21 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:13:

```
Gly Pro Lys Gly Asn Ser Gly Glu Pro Gly Ala Pro Gly Asn Lys Gly
 1           5                   10                  15
Asp Thr Gly Ala Lys
            20
```

( 2 ) INFORMATION FOR SEQ ID NO:14:

( i ) SEQUENCE CHARACTERISTICS:
  ( A ) LENGTH: 14 amino acids
  ( B ) TYPE: amino acid
  ( D ) TOPOLOGY: linear ( i i ) MOLECULE TYPE: peptide ( x i ) SEQUENCE DESCRIPTION: SEQ ID NO:14:

```
Gly Ser Lys Gly Pro Arg Gly Thr Thr Gly Pro Ala Gly Arg
 1           5                   10
```

( 2 ) INFORMATION FOR SEQ ID NO:15:

( i ) SEQUENCE CHARACTERISTICS:

5,731,409

(A) LENGTH: 16 amino acids
            (B) TYPE: amino acid
            (D) TOPOLOGY: linear (ii) MOLECULE TYPE: peptide (xi) SEQUENCE DESCRIPTION: SEQ ID NO:15:

Gly Pro Arg Gly Leu Pro Gly Glu Arg Gly Arg Pro Gly Pro Ser Gly
1               5                   10                  15

(2) INFORMATION FOR SEQ ID NO:16:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:16:

Gly Thr Pro Gly Pro Gln Gly Ile Ala Gly Asn Arg
1               5                   10

(2) INFORMATION FOR SEQ ID NO:17:

(i) SEQUENCE CHARACTERISTICS:
            (A) LENGTH: 13 amino acids
            (B) TYPE: amino acid
            (D) TOPOLOGY: linear (ii) MOLECULE TYPE: peptide (xi) SEQUENCE DESCRIPTION: SEQ ID NO:17:

Gly Ala Lys Gly Gln Pro Gly Pro Ala Gly Pro Lys Gly
1               5                   10

(2) INFORMATION FOR SEQ ID NO:18:

(i) SEQUENCE CHARACTERISTICS:
            (A) LENGTH: 15 amino acids
            (B) TYPE: amino acid
            (D) TOPOLOGY: linear (ii) MOLECULE TYPE: peptide (xi) SEQUENCE DESCRIPTION: SEQ ID NO:18:

Gly Met Lys Gly His Arg Gly Phe Ser Gly Leu Asp Gly Ala Lys
1               5                   10                  15

(2) INFORMATION FOR SEQ ID NO:19:

(i) SEQUENCE CHARACTERISTICS:
            (A) LENGTH: 12 amino acids
            (B) TYPE: amino acid
            (D) TOPOLOGY: linear (ii) MOLECULE TYPE: peptide (xi) SEQUENCE DESCRIPTION: SEQ ID NO:19:

Gly Ala Pro Gly Asp Lys Gly Leu Arg Gly Leu Thr
1               5                   10

(2) INFORMATION FOR SEQ ID NO:20:

(i) SEQUENCE CHARACTERISTICS:
            (A) LENGTH: 13 amino acids
            (B) TYPE: amino acid
            (D) TOPOLOGY: linear (ii) MOLECULE TYPE: peptide ( x i ) SEQUENCE DESCRIPTION: SEQ ID NO:20:

Gly Pro Ala Gly Lys Asp Gly Glu Ala Gly Ala Gln Gly
1               5                       10

( 2 ) INFORMATION FOR SEQ ID NO:21:

( i ) SEQUENCE CHARACTERISTICS:
      ( A ) LENGTH: 18 amino acids
      ( B ) TYPE: amino acid
      ( D ) TOPOLOGY: linear ( i i ) MOLECULE TYPE: peptide ( x i ) SEQUENCE DESCRIPTION: SEQ ID NO:21:

Gly Lys Pro Gly Arg Pro Gly Gln Arg Gly Pro Pro Gly Pro Gln Gly
1               5                       10                      15

Ala Arg

1

POLYPEPTIDES WITH TYPE I COLLAGEN ACTIVITY

GOVERNMENT SUPPORT

This invention was made with government support under contract No. AR 01929 by the U.S. Institutes of Health. The government has certain rights in the invention.

BACKGROUND OF THE INVENTION

The adhesion of mammalian cells to the extra-cellular matrix is of fundamental importance in regulating growth, adhesion, motility and the development of the proper cellular phenotype. This has implications for normal cell growth and development, wound healing, chronic inflammatory diseases, diabetes, tumor metastasis, and other physiological processes. Evidence accumulated over the last several years suggests that the molecular basis for the adhesion of both normal and transformed or malignant cells is complex and probably involves several distinct cell surface molecules. Extracellular matrices consist of three types of macromolecules: collagenous glycoproteins, proteoglycans and noncollagenous glycoproteins.

Types I, II, III, and IV collagen are among the most important structural proteins. Collagens are composed of three chains. Types II and III collagen are homotrimeric with all three chains of identical sequence. Types I and IV collagen are heterotrimeric with two chains of identical sequence and the third chain of a different sequence. The two types of chains of type I collagen are referred to as the $\alpha1(I)$ and $\alpha2(I)$ chains. Types I, II, III, and IV collagen are composed primarily of repeating Gly-X-Y triplets, which induces each chain to adopt a left-handed poly-triple-helical conformation. This conformation makes collagen a structurally unique recognition element. The interaction of cells with the unique recognition element of triple-helical collagens influences a variety of physiological processes such as tumor cell metastasis and atherosclerosis, which involves collagen mediated platelet aggregation.

Type I collagen, in particular, is involved in a variety of physiological processes through interactions with various cells and tissues. Hence, adhesion to type I collagen presents a particularly useful point at which to influence physiological processes. Adhesion of cells and tissues to type I collagen is mediated by several classes of cellular receptors for type I collagen. Studies with human fibrosarcoma cells (HT-1080) revealed two classes of heterodimeric cell surface collagen receptors. These receptors have a common β subunit but different α subunits ($\alpha2$ and $\alpha3$). The $\alpha2\beta1$ integrin mediates specific attachment of fibrosarcoma cells to types I–IV collagen. The $\alpha3\beta1$ integrin mediates adhesion to types I and IV collagen as well as to fibronectin and laminin. Human platelets have an $\alpha2\beta1$ receptor that mediates their adhesion to a region of type I collagen containing Glu or Asp in a $Mg^{2+}$ dependent manner. Platelets also adhere to collagen $\alpha1(I)$ and $\alpha2(I)$ chains in a $Mg^{2+}$ dependent manner through the $\alpha2\beta1$ integrin. In addition, platelets have an additional receptor that binds to type I collagen. This interaction is independent of divalent cations and results in platelet activation. Another cell surface glycoprotein, the class III collagen receptor (CRIII), binds to type I collagen, but is not a primary mediator of adhesion. A cell surface chondroitin sulfate proteoglycan has also been shown to play a role in type I collagen-mediated melanoma cell motility and invasion. The variety of receptors and cells illustrates the importance of interactions with type I collagen.

Not only are interactions mediated by different receptors, but the specificity of a particular receptor can be modulated as well. For example, although the $\alpha2\beta1$ integrin is recognized as a primary specific collagen receptor, there are functional differences in the specificity of $\alpha2\beta1$ from different cell types. The $\alpha2\beta1$ integrin on human endothelial, melanoma, bladder carcinoma, and alveolar carcinoma cells is used to adhere to both collagen and laminin. On human platelets, fibroblasts, and fibrosarcoma cells, however, the $\alpha2\beta1$ integrin adheres to only collagen. The $\alpha1\beta1$ integrin has been shown to be a type I collagen receptor for rat hepatocytes, rat fibroblasts, and human melanoma cells.

The interaction of type I collagen with cellular receptors has been studied by cleaving the triple-helical domain with cyanogen bromide and studying the interaction of the resulting large polypeptide fragments derived from the $\alpha1$ chain with cells and adhesion proteins. Cyanogen-bromide fragment 8, which consists of residues 124–402 of the $\alpha1$ chain of type I collagen, adheres to hepatocytes and fibroblasts and contains an adhesion site for the $\alpha1\beta1$ integrin. At least one cell adhesion site is known to exist in cyanogen-bromide fragment 3, which consists of residues 403–551 of the $\alpha1$ chain of type I collagen. Cyanogen-bromide fragment 3 adheres to hepatocytes, fibroblasts, and platelets and contains adhesion sites for $\alpha1\beta1$ and $\alpha2\beta1$ integrins. Cyanogen-bromide fragment 7, which consists of residues 552–822 of the $\alpha1$ chain of type I collagen, adheres to Chinese hamster ovary cells and fibroblasts.

As indicated above, the $\alpha1$ chain of type I collagen has been shown to be associated with interactions of a wide variety of cell types. In most instances, however, the nature of the interactions remains ill defined. For example, the sequences within cyanogen-bromide fragments 3 and 8 responsible for binding to the $\alpha1\beta1$ integrin have not been identified. In addition, cell adhesion sites have not been identified in regions of the $\alpha1$ chain triple-helical domain of type I collagen outside cyanogen-bromide fragments 3, 7, and 8. Therefore, a need exists to isolate and characterize sequences that are responsible for the wide range of biological activities associated with type I collagen. Lower molecular weight oligopeptides corresponding to these sequences would be expected to be more readily obtainable and to exhibit a narrower profile of biological activity than either type I collagen itself or the large cyanogen-bromide fragments, thus increasing their potential usefulness as therapeutic or diagnostic agents.

SUMMARY OF THE INVENTION

The present invention provides polypeptides which represent fragments of the triple-helical domain of the $\alpha1$ chain of type I collagen. The polypeptides can be prepared by conventional solid phase peptide synthesis.

The present invention includes a polypeptide having a sequence of at least about four amino acids and, preferably, at least about seven amino acids, corresponding substantially to an amino acid sequence within the triple-helical domain of type I collagen. The polypeptides promote cell adhesion and/or cell migration. In one embodiment of the invention, the polypeptide includes at least 2 charged amino acid residues. In another embodiment of the invention the polypeptide includes a close grouping of both positively and negatively charged residues. The polypeptides of the present invention exhibit cell adhesion capacity and/or mediate cell migration. The polypeptides may promote cell adhesion. These polypeptides may also promote cell migration.

The polypeptides of the invention include polypeptides that promote cell adhesion and are derived from particular fragments of the triple-helical domain of the α1 chain of type I collagen. These polypeptides include polypeptides corresponding substantially to an amino acid sequence within cyanogen-bromide fragment 3, cyanogen-bromide fragment 6, cyanogen-bromide fragment 7, or cyanogen-bromide fragment 8. A polypeptide of the invention may also be derived from portions of the triple-helical domain of the α1 chain of type I collagen outside the above mentioned cyanogen bromide fragments.

Preferred polypeptides of the invention include the polypeptide represented by SEQ ID NO:1, the polypeptide represented by SEQ ID NO:2, the polypeptide represented by SEQ ID NO:3, the polypeptide represented by SEQ ID NO:4, the polypeptide represented by SEQ ID NO:5, the polypeptide represented by SEQ ID NO:6, the polypeptide represented by SEQ ID NO:7, the polypeptide represented by SEQ ID NO:8, the polypeptide represented by SEQ ID NO:9, the polypeptide represented by SEQ ID NO:10, the polypeptide represented by SEQ ID NO:11, the polypeptide represented by SEQ ID NO:12, the polypeptide represented by SEQ ID NO:13, the polypeptide represented by SEQ ID NO:14, the polypeptide represented by SEQ ID NO:15, the polypeptide represented by SEQ ID NO:17, the polypeptide represented by SEQ ID NO:18, the polypeptide represented by SEQ ID NO:19, and the polypeptide represented by SEQ ID NO:21.

More preferred polypeptides of the invention include the polypeptide represented by SEQ ID NO:1, the polypeptide represented by SEQ ID NO:2, the polypeptide represented by SEQ ID NO:3, the polypeptide represented by SEQ ID NO:5, the polypeptide represented by SEQ ID NO:6, the polypeptide represented by SEQ ID NO:8, the polypeptide represented by SEQ ID NO:9, the polypeptide represented by SEQ ID NO:10, the polypeptide represented by SEQ ID NO:12, the polypeptide represented by SEQ ID NO:13, the polypeptide represented by SEQ ID NO:14, the polypeptide represented by SEQ ID NO:15, the polypeptide represented by SEQ ID NO:18, and the polypeptide represented by SEQ ID NO:19.

The peptides most preferred according to the invention include the polypeptide represented by SEQ ID NO:5, the polypeptide represented by SEQ ID NO:6, the polypeptide represented by SEQ ID NO:8, the polypeptide represented by SEQ ID NO:9, the polypeptide represented by SEQ ID NO:10, the polypeptide represented by SEQ ID NO:12, and the polypeptide represented by SEQ ID NO:13.

The polypeptide may be in free form or may be covalently bound to a carrier molecule as part of a polypeptide/carrier molecule conjugate.

The present invention also provides a cell culture substrate having a surface coated with at least one of the polypeptides of the invention. The cell culture substrate may be a surface which includes a synthetic resin, a portion of a bead, a portion of a macroporous fiber, or the wells of a microtiter plate.

The polypeptides of the invention may also be used in a method for distinguishing cell types. This method includes differential binding of cells to surfaces coated with a composition including one or more polypeptides of the invention. The polypeptides chosen bind to a specific type of cell or cells while other cells do not bind. Hence the occurrence of binding or lack of binding differentiates between cell types. For example, the method may be used to differentiate amongst cells such as: normal breast stromal cells, breast carcinoma cells, human melanoma cells, Jurkat cells, hepatocytes, fibroblasts, platelets, Chinese hamster ovary cells, carcinoma cells, melanoma cells, leukemia lymphatic cells, lymphatic cells, or T-cells.

In yet another embodiment of the invention, the polypeptides may also be used to identify cells. After coating a surface with a composition including at least one polypeptide of the invention, cells are contacted with the coated surface. The cells to be identified adhere to the coated surface. This method can be used to identify a variety of cancer cells including breast carcinoma cells, human melanoma cells, and human leukemia lymphatic cells. Other types of cells may be identified by this method as well. Examples of such cells include normal breast stromal cells, hepatocytes, fibroblasts, platelets, Chinese hamster ovary cells, lymphatic cells, or T-cells.

The present invention also provides a prosthetic device designed for placement in vivo. The device includes a surface coated with a composition which includes at least one of the cell adhesion promoting polypeptides described above. Typically, the coating composition includes the polypeptide in the form of a polypeptide/carrier molecule conjugate.

DETAILED DESCRIPTION OF THE INVENTION

Figure 1:
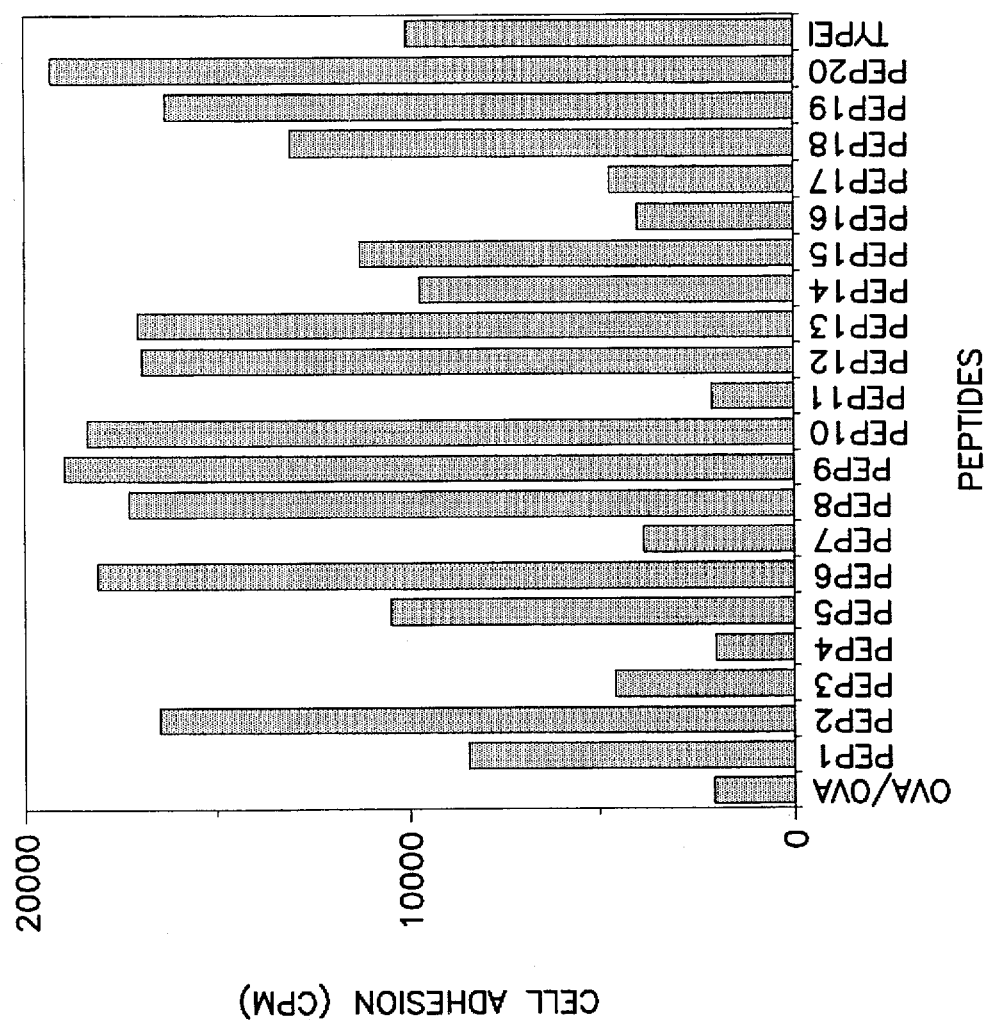
FIG. 1 is a bar chart depicting adhesion of normal breast stromal cells (Hs578Bst) to polypeptides of the invention. Adhesion of the normal breast stromal cells (Hs578Bst) to type I collagen and to ovalbumin are included as controls.

Type I collagen is composed of two chains of identical sequence and a third chain of a different sequence. These chains intertwine to adopt a domain structure with triple-helical conformation. The total number of amino acids in the triple-helical region of collagen α1(I) chains is 1014. The numbering of residues in the α1 chain of type I collagen is according to Chapman et al. in *Structural Aspects of Recognition and Assembly in Biological Macromolecules*, pp. 387–401 (1981). These triple-helical domains provide a unique recognition element in type I collagen.

Binding of polypeptides with type I collagen activity to cellular receptors is of special interest since these receptors are associated with various cellular functions such as adhesion, motility, migration, spreading, etc. It may be possible to have specific effects on these functions in different cells and tissues, since there are several classes of these cellular receptors that exert a range of effects on their host cells. This specificity is possible since the receptors may recognize different sequences within the type I collagen.

The α1 chain of type I collagen can be cleaved by cyanogen bromide to generate polypeptide fragments of type I collagen. These cyanogen bromide fragments have been numbered (see Bornstein & Traub, *The Proteins*, 3rd Ed., Vol. IV, Academic Press, N.Y., pp. 411–632 (1979)). Cyanogen bromide fragment 3 corresponds to the amino acid sequence within the triple-helical domain of the α1 chain of type I collagen from residues 403–551. Cyanogen bromide fragment 4 corresponds to the amino acid sequence within the triple-helical domain of the α1 chain of type I collagen from residues 40–86. Cyanogen bromide fragment 5 corresponds to the amino acid sequence within the triple-helical domain of the α1 chain of type I collagen from residues 87–123. Cyanogen bromide fragment 6 corresponds to the amino acid sequence within the triple-helical domain of the α1 chain of type I collagen from residues 823–1014. Cyanogen bromide fragment 7 corresponds to the amino acid sequence within the triple-helical domain of the α1 chain of type I collagen from residues 552–822. Cyanogen bromide fragment 8 corresponds to the amino acid sequence within the triple-helical domain of the α1 chain of type I collagen from residues 124–402.

Polypeptides corresponding to sequences from type I collagen may include charged amino acid residues. The charges of amino acids residues are the charges that would exist at about physiological pH. As used herein, charged amino acid residues are those with charged side chain groups. Positively charged amino acid residues include arginine (Arg) and lysine (Lys). Negatively charged amino acid residues include aspartic acid (Asp) and glutamic acid (Glu). With the exception of the terminal amino acid residues, the α-amino group or α-carboxyl group are generally linked through amide bonds at interior positions of the peptide. The α-carboxyl and α-amino groups of the terminal amino acid residues typically are not part of a covalent bond and thus are charged at physiological pH. The charges of the terminal α-amino and α-carboxy groups generally cancel when calculating the net charge of a peptide. For the purposes of this invention, the α-amino and α-carboxy groups of terminal amino acid residues are, therefore, not included in the definition of charged amino acids.

One embodiment of the invention includes a polypeptide that has a net positive charge and contains at least two charged amino acid residues. The polypeptide may include both positively and negatively charged amino acid residues.

Another embodiment of the invention includes polypeptides that contain at least 2 positively charged amino acid residues. The positively charged residues are within a sequence of about 15 amino acid residues, more preferably within a sequence of about 10 amino acid residues. The polypeptide preferably has a net positive charge.

In yet another embodiment, a polypeptide of the invention may include both positively and negatively charged amino acid residues arranged as a charge cluster. A charge cluster is an amino acid sequence of no more than about 15 residues, which includes one or more close groupings of positively and negatively charged amino acid residues. For the purposes of this invention, the term "close grouping" means an amino acid sequence of no more than about 10 amino acid residues, and preferably no more than about 7 amino acid residues, which includes at least one positively charged amino acid residue and at least one negatively charged amino acid residue. Typically, the close grouping includes two positively charged amino acid residues and one negatively charged amino acid residue occurring in the order positive, negative, positive. One or more uncharged amino acid residues may be between the positively and negatively charged amino acid residues.

The present type I collagen polypeptides are typically relatively small polypeptides, e.g., include no more than about 100 amino acid residues. The type I collagen polypeptides preferably include no more than about 50 amino acids and, most preferably, include no more than about 25 amino acids. While the present polypeptides typically represent fragments from the triple-helical domain of the α1 chain of type I collagen having sequences of at least about 9 amino acids, functionally active polypeptides having shorter amino acid sequences are within the scope of the invention. For example, polypeptides having sequences of less than 9 amino acids, e.g., polypeptides having sequences of at least about 4 and, preferably, at least about 7 amino acids, are within the scope of the present invention where such polypeptides modulate cellular adhesion and/or mediate cell migration.

Polypeptide Carrier Conjugates

The polypeptides of the present invention may be employed in a monovalent state (i.e., free polypeptide or single polypeptide fragment coupled to a carrier molecule). Often, the polypeptides are employed as conjugates of multiple polypeptide fragments bound to a carrier molecule. The carrier molecule may be a biological carrier molecule (e.g., a glycosaminoglycan, a proteoglycan, albumin or the like) or a synthetic polymer. Typically, ovalbumin, human serum albumin, other proteins, polyethylene glycol, or the like are employed as the carrier molecule. Such modifications may increase the apparent affinity or change the circulatory half-life of a polypeptide. The number of polypeptide fragments associated with or bound to each carrier molecule can be varied, but from about 4 to 8 polypeptide fragments per carrier molecule are typically obtained under standard coupling conditions.

For instance, polypeptide/carrier molecule conjugates may be prepared by treating a mixture of polypeptides and carrier molecules with a coupling agent, such as a carbodiimide. The coupling agent may activate a carboxyl group on either the polypeptide or the carrier molecule so that the carboxyl group can react with a nucleophile (e.g., an amino or hydroxyl group) on the other member of the polypeptide/carrier molecule, resulting in the covalent linkage of the polypeptide and the carrier molecule.

For example, conjugates of a polypeptide coupled to ovalbumin may be prepared by dissolving equal amounts of lyophilized polypeptide and ovalbumin in a small volume of water. In a second tube, 1-ethyl-3-(3-dimethylaminopropyl)-carbodiimide hydrochloride (EDC; ten times the amount of polypeptide) is dissolved in a small amount of water. The EDC solution was added to the polypeptide/ovalbumin mixture and allowed to react for a number of hours. The mixture may then dialyzed (e.g., into phosphate buffered saline) to obtain a purified solution of polypeptide/ovalbumin conjugate. Polypeptide/carrier molecule conjugates prepared by this method typically contain about 4 to 5 polypeptide fragments per ovalbumin molecule.

Synthesis of Polypeptide

The polypeptides of the invention may be synthesized by the solid phase method using standard methods based on either t-butyloxycarbonyl (BOC) or 9-fluorenylmethoxycarbonyl (FMOC) protecting groups. This methodology is described by G. B. Fields et al. in *Synthetic Peptides: A User's Guide*, W. M. Freeman & Company, New York, N.Y., pp. 77–183 (1992). The present polypeptides were synthesized from the sequence of the α1 chain of the major triple-helical domain of human type I collagen. These polypeptides promote cell adhesion and/or migration.

Cell Culture

Normal breast stromal cells, Hs578Bst, were obtained from the American Type Culture Collection (ATCC#10). These cells were maintained in Dulbecco's Modified Medium (DMEM) containing 10% fetal bovine serum (FBS) and 30 ng/ml epidermal growth factor (EGF). The normal breast stromal cells were passage 10. For use in adhesion studies these cells were metabolically radiolabelled by incubation overnight with 200 µCi [$^{35}$S]-methionine. On the day of the assay the labeled cells were harvested by treatment with EDTA-trypsin, the trypsin was inhibited with serum, then the cells were washed to remove this mixture. The cells were resuspended at $5 \times 10^4$ cells/ml in adhesion medium. The adhesion medium used for the breast stromal cells, Hs578BST, consisted of ATCC 47X solution containing 20 mM HEPES and 2 mg/ml sigma albumin.

Breast carcinoma cells, Hs578T, were obtained from the American Type Culture Collection (ATCC#57). These cells were maintained in DMEM supplemented with 10% FBS and 10 ng/ml bovine insulin. The breast carcinoma cells were passage 51. For use in adhesion studies these cells were metabolically radiolabelled by incubation overnight with 200 µCi [$^{35}$S]-methionine. On the day of the assay the labeled cells were harvested by treatment with EDTA-trypsin, the trypsin was inhibited with serum, then the cells were washed to remove this mixture. The washed cells were resuspended at $5 \times 10^4$ cells/ml in adhesion medium. The adhesion medium used for the breast carcinoma cells, Hs578T, consisted of DMEM supplemented with 20 mM HEPES at pH 7.2–7.4 and 2 mg/ml sigma albumin.

The invention will be further described by reference to the following detailed examples.

EXAMPLE 1

Adhesion of Normal and Tumor Cells with Peptides from Triple-Helical Domain of Type I Collagen Adhesion was tested for each polypeptide of the invention, with type I collagen, and ovalbumin as controls, using a modification of the method of Chelberg et al., *J. Cell Biol.*, 111, 261–70 (1990). The method uses wells of a 96-well microtiter plate to which the polypeptide of interest had been absorbed from 74 µL of a solution containing polypeptide at 10 ug/ml. Each polypeptide was examined individually for direct cell adhesion with normal breast stromal (Hs578Bst) cells and breast carcinoma (Hs578T) cells.

A cell suspension (100 µL/well, ~$5 \times 10^3$ cells/well) was added to each polypeptide coated well and the assay mixture was incubated at 37° C. for 30–60 min. At the end of the incubation the wells were washed 3 times with phosphate buffered saline (PBS) containing $Mg^{2+}$ and $Ca^{2+}$ to remove non-adherent cells. To detect and quantify adherent cells 150 µL of Microscint was added to each well and the $^{35}$S-labeled cells were detected in the microtiter plate using a Topcount Scintillation Counter.

The adhesion of normal breast stromal cells (Hs578Bst) to the wells of a microtiter plate coated the polypeptides (74 µL of 10 µg/ml polypeptide solution/well) is shown in FIG. 1. Most of the polypeptides of the invention promoted adhesion as well as or better than type I collagen. This group of polypeptides includes those represented by SEQ ID NO:1, SEQ ID NO:2, SEQ ID NO:5, SEQ ID NO:6, SEQ ID NO.:8, SEQ ID NO:9, SEQ ID NO:10, SEQ ID NO:12, SEQ ID NO:13, SEQ ID NO:14, SEQ ID NO:15, SEQ ID NO:18, and SEQ ID NO:19. Polypeptides represented by SEQ ID NO:4 and SEQ ID NO:11 show adhesion far below type I collagen and, in fact, show no apparent adhesion in excess of that observed with ovalbumin.

Figure 2:
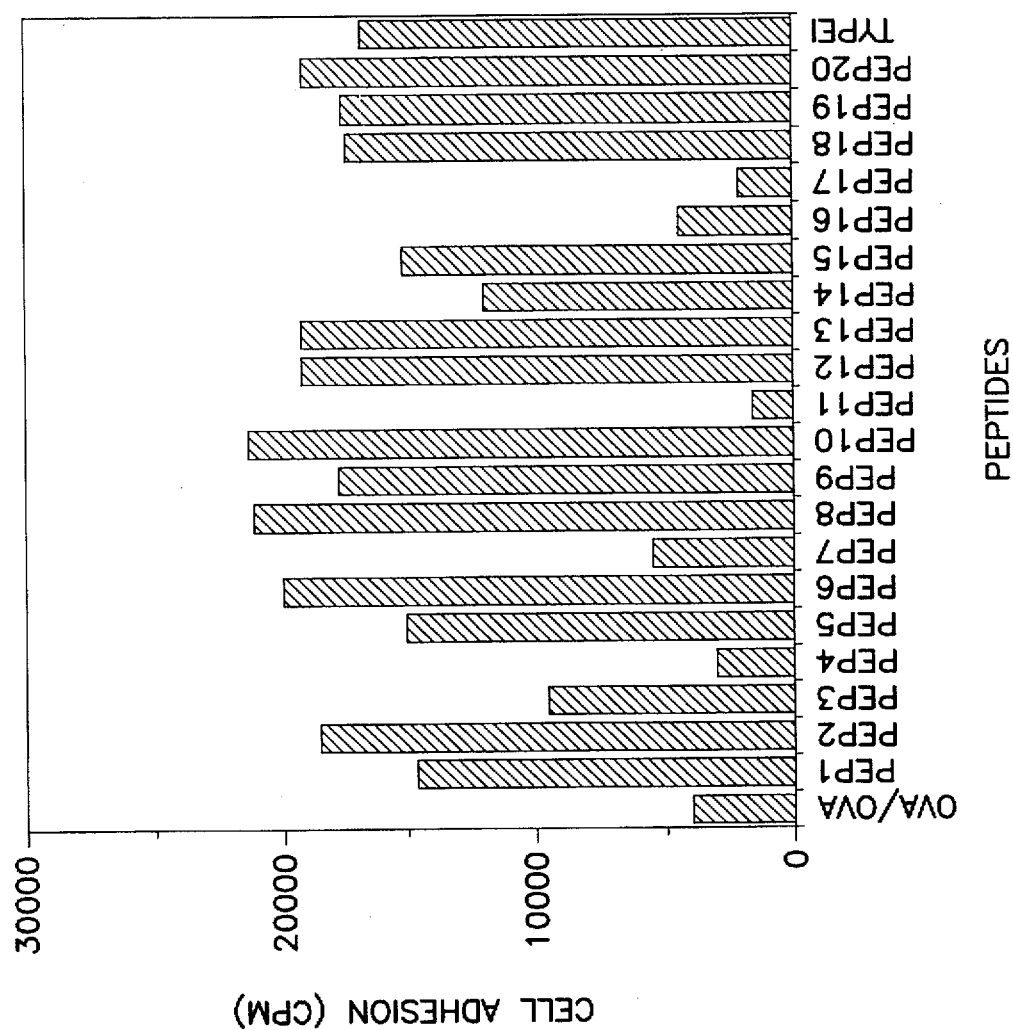
FIG. 2 is a bar chart depicting adhesion of breast carcinoma cells (Hs578T) to polypeptides of the invention. Adhesion of breast carcinoma cells (Hs578T) to type I collagen and to ovalbumin are included as controls.

The adhesion of breast carcinoma cells (Hs578T) to the polypeptides coated onto a microtiter plate (74 µL of 10 µg/ml polypeptide/well) is shown in FIG. 2. Most of the polypeptides of the invention promoted adhesion as well as or better than type I collagen. These polypeptides include those represented by SEQ ID NO:1, SEQ ID NO:2, SEQ ID NO:5, SEQ ID NO:6, SEQ ID NO:8, SEQ ID NO:9, SEQ ID NO:10, SEQ ID NO:12, SEQ ID NO:13, SEQ ID NO:14, SEQ ID NO:15, SEQ ID NO:18 and SEQ ID NO:19. Polypeptides represented by SEQ ID NO:4, SEQ ID NO:11, and SEQ ID NO:17 show adhesion far below type I collagen and, in fact, show no apparent adhesion in excess of that observed with ovalbumin.

EXAMPLE 2

Motility of Breast Stromal and Breast Carcinoma Cells with Peptides from Triple-Helical Domain of Type I Collagen Using breast stromal cells (Hs578Bst) and breast carcinoma cells (Hs578T), polypeptides of the invention and type I collagen as a control, were examined for their ability to directly mediate cell motility by a modification of the method of Chelberg et al., *J. Cell Biol.*, 111, 261–70 (1990). Peptide-mediated cell motility was assayed in 48-well microchemotaxis chambers using 8 µm pore polyvinyl pyrrolidone-free polycarbonate filters. The lower wells of the microchemotaxis chambers were filled with polypeptides dissolved in motility medium. The motility medium used for studies of the normal breast stromal cells (Hs578Bst) consisted of ATCC 47X solution supplemented with 20 mM Hepes. The motility medium used for studies of the breast carcinoma cells (Hs578T) consisted of DMEM supplemented with 20 mM HEPES at pH 7.2–7.4. Peptide was absorbed to the membrane by chemotaxis.

Cells were labeled and harvested as described above for studies of adhesion. The cells were suspended to final concentration of $4 \times 10^5$ cells/ml in motility medium. Cells were added to the upper wells at $2 \times 10^4$ cells/well and incubated for 6 hr at 37° C. Migration to the underside of the filter was then measured with a Zeiss microscope and an Optomax Image System IV.

Figure 3:
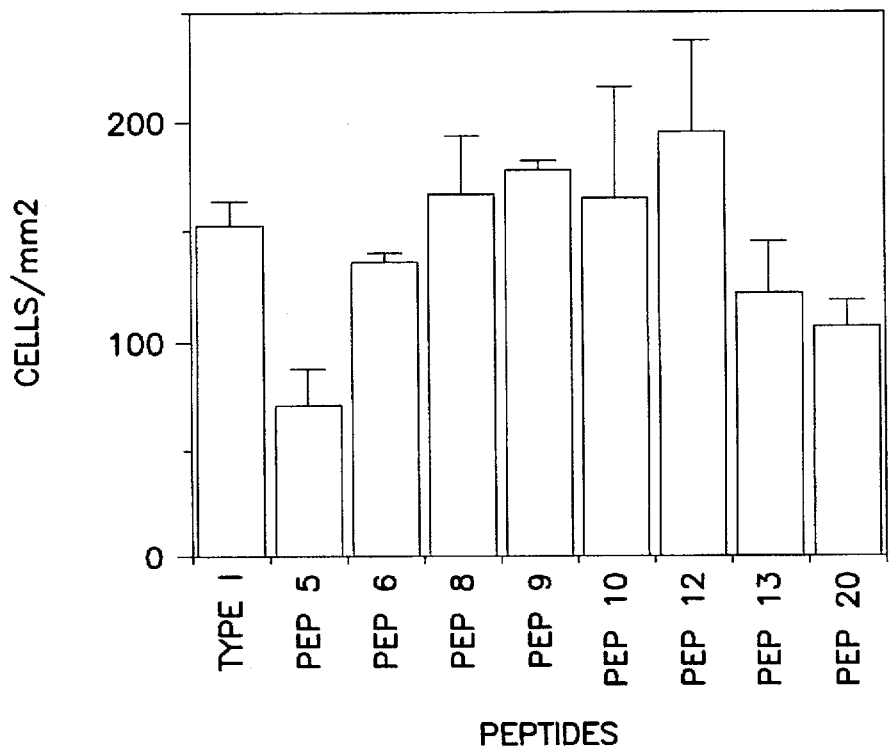
FIG. 3 is a bar chart depicting motility of normal breast stromal cells (Hs578Bst) mediated by polypeptides of the invention. Motility of normal breast stromal cells (Hs578Bst) mediated by type I collagen is included as a control.

FIG. 3 illustrates the polypeptide mediated motility of normal breast stromal cells (Hs578Bst). The polypeptides tested mediated cell motility to an extent nearly as great as type I collagen. These peptides include those represented by SEQ ID NO:5, SEQ ID NO:6, SEQ ID NO:8, SEQ ID NO:9, SEQ ID NO:10, SEQ ID NO:12, SEQ ID NO:13, and SEQ ID NO:20.

Figure 4:
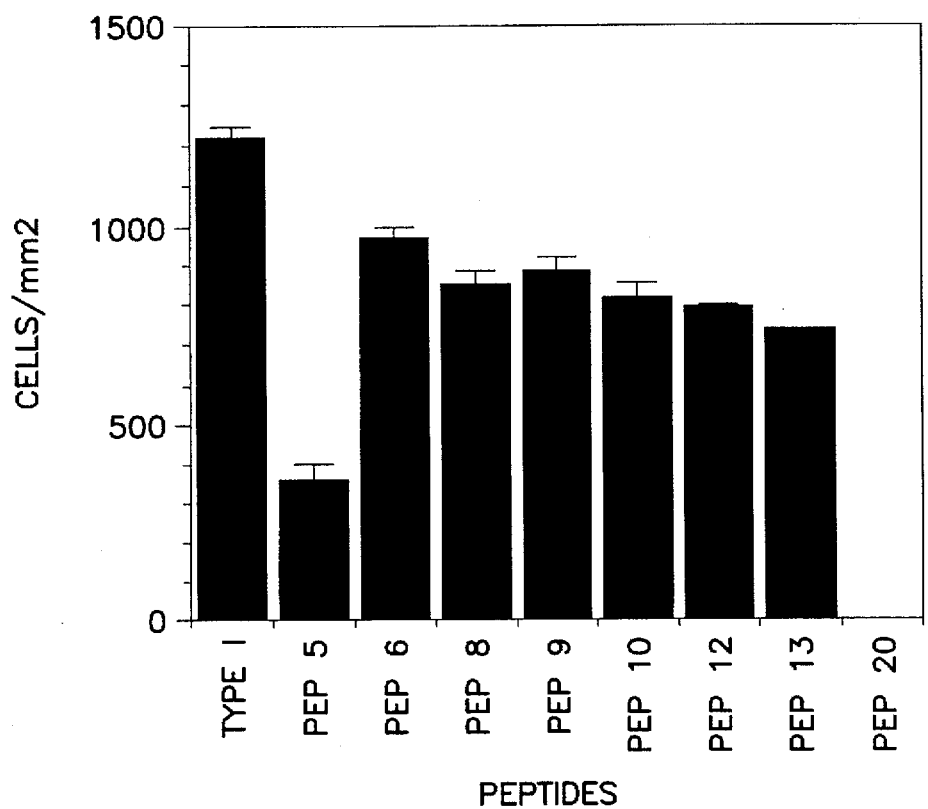
FIG. 4 is a bar chart depicting the motility of breast carcinoma cells (Hs578T) mediated by polypeptides of the invention. Motility of breast carcinoma cells (Hs578T) mediated by type I collagen is included as a control.

FIG. 4 illustrates the polypeptide mediated motility of breast carcinoma cells (Hs578T). Most of the polypeptides tested mediated cell motility to an extent nearly as great as or in excess of type I collagen. These peptides include those represented by SEQ ID NO:5, SEQ ID NO:6, SEQ ID NO:8, SEQ ID NO:9, SEQ ID NO:10, SEQ ID NO:12 and SEQ ID NO:13. Motility was apparently not promoted by the polypeptide represented by SEQ ID NO:20.

These examples demonstrate that a number of the polypeptides of the invention promote the adhesion and/or migration of normal breast stromal and breast carcinoma cells. In addition, differential effects on motility of normal breast stromal and breast carcinoma cells were observed.

This might reflect the variety of cellular receptors that recognize the polypeptides.

A number of the practical applications for the polypeptides of the present invention can be envisioned. Such applications include the promotion of the healing of wounds caused by the placement of synthetic substrata within the body. Such synthetic substrata can include artificial vessels, intraocular contact lenses, hip replacement implants and the like, where cell adhesion is an important factor in the acceptance of the synthetic implant by normal host tissue.

As described in U.S. Pat. No. 4,578,079, medical devices can be designed making use of these polypeptides to attract cells to the surface in vivo or even to promote the growing of a desired cell type on a particular surface prior to grafting. An example of such an approach is the induction of endothelial cell growth on a prosthetic device such as a blood vessel, heart valve or vascular graft. Such a device is generally woven or knitted from nitrocellulose or polyester fiber, particularly Dacron TM (polyethylene terephthalate) fiber. A variety of cells are attracted to type I collagen and to the present polypeptides. The latter point indicates the potential usefulness of these defined polypeptides in coating a patch graft or the like for aiding wound closure and healing following an accident or surgery. The coating and implantation of synthetic polymers may also assist in the regeneration of nerves following crush traumas, e.g., spinal cord injuries.

In such cases, it may be advantageous to couple the peptide to a biological molecule, such as albumin, a glycosaminoglycan or a proteoglycan. It is also indicative of their value in coating surfaces of a prosthetic device which is intended to serve as a temporary or semipermanent entry into the body, e.g., into a blood vessel or into the peritoneal cavity, sometimes referred to as a percutaneous device. Such devices include controlled drug delivery reservoirs or infusion pumps.

Also, the polypeptides of the present invention can be used to promote cell adhesion of various cell types to a naturally occurring or artificial substrate intended for use in vitro. For example, a culture substrate such as the wells of a microtiter plate or the medium contacting surface of microporous fibers or beads, can be coated with the cell-attachment polypeptides. This can obviate the use of type I collagen in the medium, thus providing better defined conditions for the culture as well as better reproducibility.

As one example of commercial use of cell attachment surfaces, Cytodex particles, manufactured by Pharmacia, are coated with gelatin, making it possible to grow the same number of adherent cells in a much smaller volume of medium than would be possible in dishes. The activity of these beads is generally dependent upon the use of coating protein in the growth medium and the present polypeptides are expected to provide an improved, chemically defined coating for such purposes. Other surfaces or materials may be coated to enhance attachment, such as glass, agarose, synthetic resins or long-chain polysaccharides.

A surface coated with a polypeptide may also be employed to identify cells. For example, fluids containing cells could be contacted with such a surface. Cells including the cells of interest will adhere to the surface. The adhered cells of interest may then be identified, such as by using a labeled antibody specific for a marker on the cell of interest. For example, breast carcinoma cells that bind to a polypeptide of the invention could be identified by such a method. In addition, binding of a cell to one or more of the polypeptides of the invention may be characteristic of the cell type, and the pattern of binding to a number of the polypeptides could be used to identify a particular cell type.

The invention has been described with reference to various specific and preferred embodiments and techniques. However, it should be understood that many variations and modifications may be made while remaining within the spirit and scope of the invention.

The publications and patent applications cited in this specification are indicative of the level of ordinary skill in the art to which this invention pertains. All publications and patent applications are herein incorporated by reference to the same extent as if each individual publication or patent application was specifically and individually indicated by reference.

TABLE 1

Synthetic Peptides Derived From Type I Collagen

| Collagen Chain α1 Residues | Cyanogen-Bromide Fragment | Sequence[a] | Net Charge | Positive/ Negative Charged Residues[b] | SEQ ID NO |
|---|---|---|---|---|---|
| 406–420 | 3 | GPKGAAGEPGKP | +1 | 2/1 | 1 |
| 289–300 | 8 | GKRGARGEPGPA | +2 | 3/1 | 2 |
| 496–510 | 3 | GARGERGFPGERGVQ | +1 | 3/2 | 3 |
| 679–690 | 7 | GAPGPKGARGSA | +2 | 2/0 | 4 |
| 724–735 | 7 | GKEGSKGPRGTT | +2 | 3/1 | 5 |
| 847–858 | 6 | GRDGAAGPKGDR | +1 | 3/2 | 6 |
| 349–363 | 8 | GRPGEAGLPGAKGLT | +1 | 2/1 | 7 |
| 562–573 | 7 | GAKGDRGDPGPK | +1 | 3/2 | 8 |
| 925–933 | 6 | GDRGMKGHR | +2 | 3/1 | 9 |
| 877–888 | 6 | GPVGPAGKNGDR | +1 | 2/1 | 10 |
| 385–399 | 8 | GRPGPAGPPGARGQA | +2 | 2/0 | 11 |
| 904–918 | 6 | GARGPAGPQGPRGDK | +2 | 3/1 | 12 |
| 250–270 | 8 | GPKGNSGEPGAPGNKGDTGAK | +1 | 3/2 | 13 |
| 727–740 | 7 | GSKGPRGTTGPAGR | +3 | 3/0 | 14 |
| 124–139 | 8 | GPRGLPGERGRPGPSG | +2 | 3/1 | 15 |
| 769–780 | 7 | GTPGPQGIAGNR | +1 | 1/0 | 16 |
| 97–109 | 5 | GAKGQPGPAGPKG | +2 | 2/0 | 17 |
| 85–99 | 4 + 5 | GMKGHRGFSGLDGAK | +2 | 3/1 | 18 |
| 577–588 | 7 | GAPGDKGLRGLT | +1 | 2/1 | 19 |
| 430–442 | 3 | GPAGKDGEAGAQG | −1 | 1/2 | 20 |

TABLE 1-continued

Synthetic Peptides Derived From Type I Collagen

| Collagen Chain α1 Residues | Cyanogen-Bromide Fragment | Sequence[a] | Net Charge | Positive/ Negative Charged Residues[b] | SEQ ID NO |
|---|---|---|---|---|---|
| 58–75 | 4 | GKPGRPGQRGPPGPQGAR | +4 | 4/0 | 21 |

[a]One letter codes used for amino acids are A = Ala, D = Asp, E = Glu, F = Phe, G = Gly, H = His, K = Lys, L = Leu, N = Asn, P = Pro, Q = Gln, R = Arg, S = Ser, T = Thr, V = Val.
[b]Does not include charges of α-amino or α-carboxyl groups of terminal amino acid residues.

---

What is claimed is:

1. A polypeptide having no more than about 100 amino acid residues and comprising an amino acid sequence within a triple-helical domain of an 1 chain of type I collagen, wherein said polypeptide promotes cell adhesion and said amino acid sequence is selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:17. SEQ ID NO:18, SEQ ID NO:19, and SEQ ID NO:21.

2. The polypeptide of claim 1 wherein the polypeptide has no more than about 50 amino acid residues.

3. The polypeptide of claim 1 wherein the polypeptide has no more than about 25 amino acid residues.

4. The polypeptide of claim 1 wherein the polypeptide includes an amino acid sequence selected from the group consisting of SEQ ID NO:5, SEQ ID NO:6, SEQ ID NO:8, SEQ ID NO:9, SEQ ID NO:10, SEQ ID NO:12, and SEQ ID NO:13.

5. The polypeptide of claim 1 wherein the polypeptide has an amino acid sequence selected from the group consisting of SEQ ID NO:1, SEQ ID NO:2, SEQ ID NO:5, SEQ ID NO:6, SEQ ID NO:8, SEQ ID NO:9, SEQ ID NO:10, SEQ ID NO:12, SEQ ID NO:13, SEQ ID NO:14, SEQ ID NO:15, SEQ ID NO:18, and SEQ ID NO:19.

6. The polypeptide of claim 1 wherein the polypeptide has an amino acid sequence selected from the group consisting of SEQ ID NO:1 and SEQ ID NO:3.

7. The polypeptide of claim 1 wherein the polypeptide has an amino acid sequence selected from the group consisting of SEQ ID NO:6, SEQ ID NO:9, SEQ ID NO:10, and SEQ ID NO:12.

8. The polypeptide of claim 1 wherein the polypeptide has an amino acid sequence selected from the group consisting of SEQ ID NO:5, SEQ ID NO:8, SEQ ID NO:14, and SEQ ID NO:19.

9. The polypeptide of claim 1 wherein the polypeptide has an amino acid sequence selected from the group consisting of SEQ ID NO:2, SEQ ID NO:13, and SEQ ID NO:15.

10. The polypeptide of claim 1 wherein the polypeptide has the amino add sequence of SEQ ID NO:18.

11. A polypeptide having no more than about 50 amino acid residues and comprising an amino acid sequence within a triple-helical domain of and α1 chain of type I collagen, wherein said polypeptide promotes cell migration and said amino acid sequence is selected from the group consisting of SEQ ID NO:5, SEQ ID NO:6, SEQ ID NO:8, SEQ ID NO:9, SEQ ID NO:10, SEQ ID NO:12, and SEQ ID NO:13.

12. The polypeptide of claim 11 wherein the polypeptide has no more than about 25 amino acid residues.

13. The polypeptide of claim 12 having the amino add sequence of SEQ ID NO:5.

14. The polypeptide of claim 12 having the amino add sequence of SEQ ID NO:6.

15. The polypeptide of claim 12 having the amino add sequence of SEQ ID NO:8.

16. The polypeptide of claim 12 having the amino add sequence of SEQ ID NO:9.

17. The polypeptide of claim 12 having the amino add sequence of SEQ ID NO:10.

18. The polypeptide of claim 12 having the amino add sequence of SEQ ID NO:12.

19. The polypeptide of claim 12 having the amino add sequence of SEQ ID NO:13.

20. A polypeptide/carrier molecule conjugate comprising a carrier molecule covalently linked to at least one polypeptide, wherein said polypeptide promotes cell migration, has no more than about 100 amino acid residues and includes an amino acid sequence selected from the group consisting of SEQ ID NO:5, SEQ ID NO:6, SEQ ID NO:8, SEQ ID NO:9, SEQ ID NO:10, SEQ ID NO:12, and SEQ ID NO:13.

21. The polypeptide/carrier molecule conjugate of claim 20 wherein the carrier molecule includes a biological carrier molecule.

22. The polypeptide/carrier molecule conjugate of claim 20 including at least two polypeptides having a same amino add sequence.

23. The polypeptide/carrier molecule conjugate of claim 20 including at least two polypeptides having different amino acid sequences.

24. A polypeptide/carrier molecule conjugate comprising a carrier molecule covalently linked to at least one polypeptide, wherein said polypeptide promotes cell adhesion, has no more than about 100 amino acid residues and includes an amino acid sequence selected from the group consisting of SEQ ID NO:1, SEQ ID NO:2, SEQ ID NO:3, SEQ ID NO:5, SEQ ID NO:6, SEQ ID NO:7, SEQ ID NO:8, SEQ ID NO:9, SEQ ID NO:10, SEQ ID NO:12, SEQ ID NO:13, SEQ ID NO:14, SEQ ID NO:15, SEQ ID NO:16, SEQ ID NO:17, SEQ ID NO:18, SEQ ID NO:19, and SEQ ID NO:21.

* * * * *

UNITED STATES PATENT AND TRADEMARK OFFICE
CERTIFICATE OF CORRECTION

PATENT NO. : 5,731,409
DATED : MARCH 24, 1998
INVENTOR(S) : FIELDS ET AL.

It is certified that error appears in the above-identified patent and that said Letters Patent is hereby corrected as shown below:

Title page, [56] References Cited, Other Publications: insert the following references:

Berman et al., *Biochem. and Biophys. Res. Commun.*, 194, 351 (1993).

Davis, *Biochem. and Biophys. Res. Commun.*, 182, 1025 (1992).

Morton et al., *Biochem J.*, 299, 791 (1994).

Perris et al., *J. Cell Sci.*, 106, 1357 (1993).

Qian et al., *FASEB J.*, 7, A1306 (1992).

Saelman et al., *Blood*, 82, 3029 (1993).

San Antonio et al., *J. Cell Biol.*, 125, 1179 (1994).

Staatz et al., *J. Biol. Chem.*, 265, 4778 (1990).

Col. 19, line 26: "1" should read -- $\alpha 1$ --

Col. 19, line 62: "add" should read --acid--

Col. 19, line 65: "and" should read --an--

Col. 20, lines 26, 28, 30, 32, 34, 36, 38, 52: In all instances "add" should read --acid--

Signed and Sealed this

Third Day of August, 1999

Attest:

Attesting Officer

Q. TODD DICKINSON

Acting Commissioner of Patents and Trademarks